United States Patent [19]

Rijke et al.

[11] 4,141,864

[45] Feb. 27, 1979

[54] OSSEOUS CEMENT COMPOSITION

[75] Inventors: Arie Rijke, Velsen, Netherlands; Sue McCoy, Gordonsville; Robert E. McLaughlin, Charlottesville, both of Va.

[73] Assignee: University of Virginia Alumni Patents Foundation, Charlottesville, Va.

[21] Appl. No.: 861,295

[22] Filed: Dec. 16, 1977

Related U.S. Application Data

[63] Continuation of Ser. No. 451,480, Mar. 15, 1974, abandoned.

[51] Int. Cl.$^2$ .................... A61K 5/06; C08L 33/10
[52] U.S. Cl. ................... 260/17.4 SG; 32/12; 128/92 G; 260/8; 260/42.53; 521/63
[58] Field of Search ............ 260/2.5 R, 2.5 M, 8, 260/17.4 SG, 42.53, ; 106/35; 32/12; 128/92 G

[56] References Cited

U.S. PATENT DOCUMENTS

| 2,347,567 | 4/1944 | Kresse | 32/12 |
|---|---|---|---|
| 3,215,137 | 11/1965 | Laakso | 260/17.4 SG |
| 3,629,187 | 12/1971 | Weller | 32/15 |
| 3,639,312 | 2/1972 | Turner | 260/17.4 SG |
| 3,787,900 | 1/1974 | McGee | 32/12 |
| 3,789,029 | 1/1974 | Hodosh | 260/2.5 R |
| 3,810,938 | 5/1974 | Schmitt et al. | 106/35 |
| 3,867,329 | 2/1975 | Halpern et al. | 260/17.4 SG |

FOREIGN PATENT DOCUMENTS 1248165  3/1976  United Kingdom.

OTHER PUBLICATIONS

Mitchell, A Textbook in Biochemistry, 1st Edition, 1946, pp. 500–503 and 530–534.
Lavelle and Johnson, Polymer Composites for use in Orthopedic Surgery, Journal of Biomechanics, vol. 6, No. 6, Nov. 1973, pp. 651–655.

*Primary Examiner*—Allan Lieberman
*Attorney, Agent, or Firm*—Oblon, Fisher, Spivak, McClelland & Maier

[57] ABSTRACT

An osseous cement for orthopedic or dental application, which comprises the admixture of 10 to 40% weight of organic or inorganic particles wherein said particles are soluble in the extracellular fluid of the body, and are essentially non-toxic, 20 to 40% weight of an acrylic monomer and 35 to 65% weight of an insoluble particulate filler having a particle size of less than 100μ.

6 Claims, 2 Drawing Figures

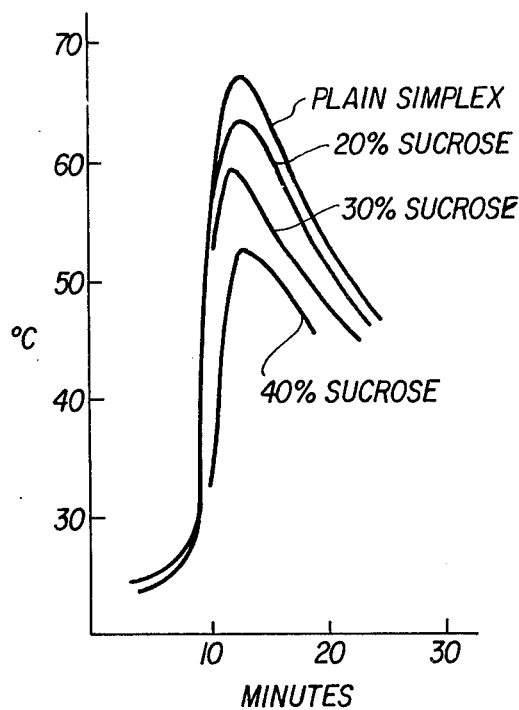
FIG. 1 CURING TEMPERATURE OF SUCROSE + SIMPLEX (TOTAL AMOUNT REMAINED CONSTANT)
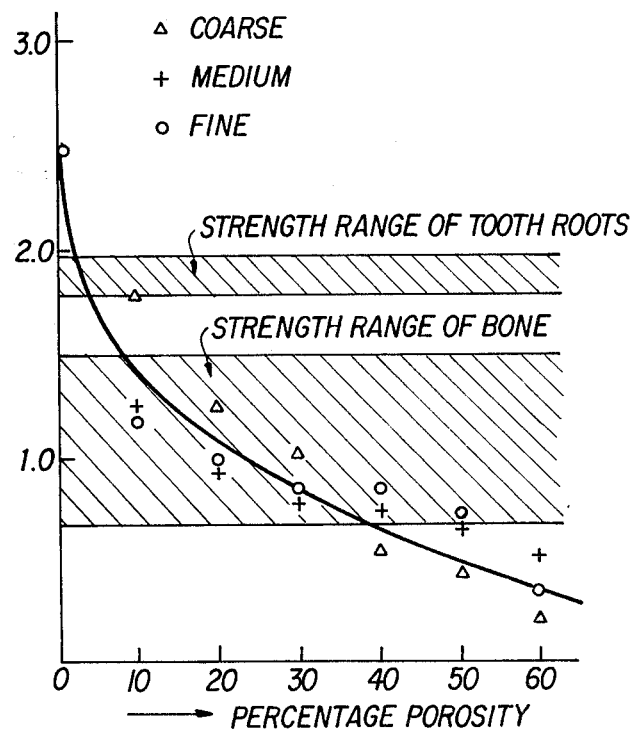
FIG. 2 STRENGTH OF POROUS ACRYLIC PLUGS

OSSEOUS CEMENT COMPOSITION

The Government has rights in this invention pursuant to grant GU-1531 awarded by the National Science Foundation.

This is a continuation of application Ser. No. 451,480 filed Mar. 15, 1974, and now abandoned.

BACKGROUND OF THE INVENTION

1. Field of the Invention

This invention relates to a cement which can be used for repair of osseous structures, fixation of implants, and in particular as a dental or orthopedic cement.

2. Description of the Prior Art

Considerable research effort has been directed to providing cements which have adhesion for, and can be used for repairing human and animal bones or teeth. Although a wide variety of different cement compositions has been proposed for this purpose, the most successful are the acrylic cements, particularly those cements derived from polymers of methyl or ethyl acrylate, or methacrylate.

In the usual method, a metal implant or pin is inserted into the bone which is held in place by the use of a cement which bonds the implant to the adjacent bone. The acrylic monomer cements generally consist of a relatively thick paste or organosol of polymer powder and a low temperature polymerization initiator dispersed into the liquid monomer.

Several severe difficulties, however, have now been encountered which threaten to significantly hinder the full development of this technique. For one, the polymerization of the acrylic monomer is accompanied by the evolution of a considerable amount of exothermal heat which reportedly has been responsible for the development of bone temperatures as high as 83° C. using conventional orthopedic cements. [See for instance, Homsy, C. A., *Prosthesis Seating Compounds of Rapid Cure Acrylic Polymers*, National Academy of Sciences — American Academy, *Orthopedic Surgery*, Joint Workshop on Total Hip Replacement and Skeletal Attachment (Nov. 6, 1969), and Bloch et al, *Evaluation of Cold-Curing Acrylic Cement for Prosthesis Stabilization*, Clin. Orthopaedics 72, 239 (1970).]

This high heat evolution has deleteriously resulted in necrosis of the surrounding bone tissue [See Wiltse et al, *Experiment Studies Regarding the Possible Use of Self-Curing Acrylics in Orthopedic Surgery*, J. Bone Joint Surg. 35A, 961 (1957).]

Another difficulty encountered has been the observation that a small amount of unreacted acrylic monomer invariably leaves the bonding area and is released into the general circulatory system. Since the acrylic monomers are quite toxic, even in relatively low concentration, this is now recognized as a considerable difficulty which threatens the continued usage of this technique.

A still further difficulty encountered, is that the long-term adhesion of the cement is disappointingly low, so that frequently the implant has been loosened, which resulted in the necessity of further surgical procedures. Methods therefore have been sought to improve the long-term adhesiveness of the cement.

The implant technique for orthopedic and certain dental procedures was first developed by Charnley, *A Biomedical Analysis of the Use Of Cement to Anchor the Femoral Head Prosthesis*, J. Bone Joint Surg. 47B 354 (1965). At that time, Charnley recognized that the success of the technique depended upon the smooth transition from implant to bone through a thin layer of fibrous tissue. If the thin fibrous tissue layer fails to develop, loose prosthesis can occur, which can result in bone erosion or migration.

To overcome this difficulty, it has been attempted to provide means to promote the growth of the fibrous tissue. Several orthopedic surgeons have attempted to fabricate prosthetic bone implants having a configuration of natural bone, i.e., composed of a network into which the tissue can grow. Incorporating pores in ceramic material has been successful in that the growth of fibrous tissue and natural bone into the implant can occur. By incorporating pores in ceramic materials, the ingrowth of fibrous tissue followed by ossification has been observed to occur, provided the pores are continuous and large enough to accommodate blood vessels. The resulting bone ingrowth can then rearrange along the stress lines. [See Hulbert et al, *Potential of Ceramic Materials as Permanently Implantable Skeletal Prosthesis*, Second Materials Engineering Conference, National Meeting of AlCh.E (1970)].

However, all of the currently available implants are pre-formed and thus do not fit exactly into the bones in which they are implanted, necessitating the use of a cement to hold them in place. The previously available cements, however, tended to destroy the available porosity into which tissue could grow.

Although certain of these difficulties have been partially overcome in the prior art, no prior art technique suggested has been found to overcome all of these difficulties.

For instance, it is the recognition of this invention, as will be explained below, that the incorporation of an adequate amount of particulate water soluble materials will provide a cement with a sufficient porosity through which the fibrous tissue can grow to strengthen the implant-to-tissue bond. The mere incorporation of a soluble chemical into acrylate polymers such as polymethylmethacrylate to provide porosity has been disclosed in U.S. Pat. No. 2,347,567. In that reference, however, the monomer and a germicide in crystalline form are charged into a mold in which polymerization is effected to form a surgical implant. The implant is formed in the shape of a screw which is screwed into the bone. In turn, the body fluid dissolves the crystalline germicide so that a porous structure is obtained into which osseous bridges can be formed. This is unlike the present invention which is concerned with the formation of a cement which is used to fix the implant, and not to the implant per se. In the present invention the particles are incorporated into the monomer or partially polymerized resin to form a cement which is polymerized in the body — not in a mold. The particles then function not only to provide a porous bond interface, but, as will be explained below, also to prevent thermal necrosis of surrounding bone tissue, and to prevent out-migration of the monomer. Moreover, the product of this patent was germicidal crystals which would burn the surrounding tissues, and hence would be detrimental for implant purposes. That is, germicidal crystals would be toxic to the surrounding tissue, and hence unsuitable. Moreover, some of the germicide will invariably remain in the mixture after the germicide has become leached out, which would prevent growth of tissue into the pores of the cement. One object of the present invention, as described in detail below, is to provide for tissue growth into the osseous cement, and thereby improve the longevity of the bond.

U.S. Pat. No. 3,215,137 discloses the use of sucrose esters as a liquid diluent to prevent excessive heat generation during polymerization of methylmethacrylate, which is used for immobilizing bandages for fractured limbs; however, soluble particles are not used, and the use contemplated is outside the body and not internal.

None of these references suggest a method of simultaneously providing a cement which permits the ingrowth of tissue so as to provide a high strength porous bond, elimination of monomer toxicity, and elimination of thermal necrosis.

Accordingly, a need exists for a cement which can be used for orthopedic and dental applications, which does not release toxic quantities of monomer into the general circulatory system, which does not cause thermal necrosis during polymerization and hardening, and which provides a porous high strength interface as a result of tissue ingrowth.

SUMMARY OF THE INVENTION

Accordingly, one object of this invention is to provide an orthopedic or dental cement composition which provides a porous, yet high strength bond joint.

Another object of this invention is to provide an orthopedic or dental composition which minimizes the release of toxic quantities of monomer into the general circulatory system during its polymerization or hardening phase.

A further object of this invention is to provide an orthopedic or dental cement composition which can be polymerized or hardened without the development of large quantities of exothermal heat which might cause thermal necrosis of surrounding tissues.

A further object of this invention is to provide a method for joining fractured bones or teeth without introduction into the body of deleterious amounts of monomer, without generation of damaging levels of exothermic heat and in high strength, which method will provide a bond of porous cement through which fibrous tissues can grow to further strengthen the bond.

These and other objects of the invention as will hereinafter become readily apparent as the discussion proceeds, can be attained by providing an osseous cement which comprises the admixture of 10 to 40% weight of organic or inorganic particles wherein said particles are soluble in the extracellular fluid of the body, and are essentially non-toxic, 20 to 40% weight of an acrylic monomer and 35 to 65% weight of an insoluble particulate filler having a particle size of less than 100μ. Throughout the specification the word, "soluble", is used to refer to those particles which are sufficiently soluble in the extracellular fluid of the body to be leachable from the osseous cement prepared from the composition which contains said particles.

DETAILED DESCRIPTION OF THE INVENTION

According to this invention, soluble organic or inorganic particles are admixed with a polymerizable acrylic monomer and a polymerization initiator and an accelerator.

In the conception of this invention, the intended purpose of including soluble particles in the cement was to provide a method of rendering the cement bond sufficiently porous that fibrous tissue could grow through the cement layer and thereby ultimately provide a stronger bond between either the bond parts or between a bone part and an implant used to secure the bone parts. The intention was that after the cement had been hardened, the soluble particles contained therein would be leachable, leaving a porous bond interface. Moreover, an equally important result occurred as a consequence of incorporating the soluble particles into the cement. The large surface area of the soluble particles absorb quantities of liquid monomer which can therefore no longer escape from the implantation site to the central circulation. Since the soluble particles are in adjacent proximity to the bulk of the polymerizing acrylic monomer, the monomer adsorbed to the particles polymerizes with the remaining monomer and is prevented from leaving the bond site. However, the particles continue to be leachable so that the final bond structure is porous. It would have been surmised that the coating of the polymerized monomer onto the surface of the particles would prevent the body fluids from leaching the soluble particles, however, this did not occur.

The presence of the particles also provides a still further effect in that they act as a heat sink for the exothermic heat generated by the polymerization reaction. The heat generated therefore is expended in raising the relatively high heat capacity particles, and therefore, no significant thermal necrosis occurs to the surrounding bond tissue. Moreover, the presence of the particles dilutes the quantity of monomer required so that less exothermic heat is generated.

Another unexpected result of this invention is the discovery that, although it was expected that the presence of the pores in the bond interface would weaken the bond strength until the fibrous tissue could grow through the interface, in fact, the bond was almost as strong as if the pores were not induced. The result is therefore, that cement with a continuous pore system is formed which allows tissue ingrowth which further strengthens the bond and improves longevity.

The result of the introduction of the soluble particles into the acrylic cement is therefore that thermal necrosis is substantially eliminated, the introduction of toxic quantities of monomer into the circulatory system is severely curtailed, and a bond is formed which is characterized by a high strength and a high degree of porosity, which permits the growth of fibrous tissue through the interface.

The particles used for the purposes of this invention may be of any chemical composition, organic or inorganic, so long as they conform to the following criteria.

1. The particles must be soluble in the extracellular fluid which surrounds the bonding site so that they may be leached from the cement to provide a porous interface.

2. The particles must have essentially the same pH as the extracellular fluid so that no shift in pH of the fluid is induced.

3. The particles must have substantially no effect on the ionic strength of the extracellular fluid.

4. The particles must be non-toxic, which also implies non-carcinogenic and non-antigenic.

5. The particles must be hard and essentially non-deformable otherwise they may not be sufficient to maintain the proper size porosity.

6. The particles must be in the form of particles of 50 to 250μ (average) and, preferably 100 to 200μ. Much larger particles sizes will tend to require undesirably large quantities of soluble particles to assure continuous porosity and also discourage tissue ingrowth, whereas smaller average diameters will tend to hinder the growth of fibrous tissue through the bond interface.

7. The particles must not melt below or near the curing temperature of the cement, since otherwise they would lose their shape during the cement application.

8. It is preferable that the particles not swell in or imbibe monomer or body fluids when heated to curing temperature, since swelling or dissolution could fracture the implant or could crack the cement.

Particles which meet these criteria include particles of non-ionic compounds, such as monosaccharides such as glucose, fructose, xylose, mannose, fucose, galactose or the like; the disaccharides, such as sucrose, lactose, maltose, or the like; the higher soluble mers, such as oligosaccharides; the metabolites, such as amino acids; or salts or esters of inorganic or organic acids including the buffer salts and hydrated forms, such as calcium glycerate, sodium fumarate, calcium isovalerate, calcium citrate, calcium succinate, calcium fumarate, $CaCO_3 \cdot MgCO_3$, calcium laurate, calcium glycerophosphate, calcium lactate, calcium saccharate, calcium salicylate, calcium carbonate, tricalcium phosphate, hydroxyapatite, and calcium gluconate.

The particular chemical composition of the particles is not critical so long as they meet the above criteria.

Suitable acrylic monomers which may be used in forming the cement include acrylic acid, methyl-acrylate, methyl methacrylate, ethyl acrylate, ethyl methacrylate, propyl acrylate, butyl acrylate, propyl methacrylate and higher alkyl acrylate and methacrylate homologs; methyl- ethyl-, and propyl-α-haloacrylates and higher alkyl homologs thereof wherein halo includes chloro, bromo, fluoro, and iodo; hydroxymethyl-methacrylate; halomethyl methacrylate, haloethyl methacrylate and halopropyl methacrylate and the like; hydroxymethyl methacrylate, hydroxyethyl methacrylate, hydroxypropyl methacrylate and the like; hydroxymethyl acrylate, hydroxyethyl acrylate, hydroxypropyl acrylate and the like; and halomethyl acrylate, haloethyl acrylate, halopropyl acrylate, as well as mixtures and copolymers of the above monomers. Suitable contents can be formed from copolymers of any of the above monomers with styrene and derivatives thereof such as α-methylstyrene, vinyl acetate, vinyl halides, vinylidene halides, alkyl vinyl ethers and ethylene derivatives.

The quantity of particles used in this composition is 10 to 40% by weight, and preferably 25 to 35% by weight based on the weight of the total composition.

In general, the quantity of particles and the size of the particles are selected such that the probability of the particles touching is quite high. After leaching, therefore, the resulting polymer product will have a continuous porous structure. In this manner, a significant proportion of the pores will extend from one side of the cement to the other.

The minimum size of the particles is such that the growth of fibrous tissue is not hindered by the size of the resulting pores. The maximum size of the soluble particles is such that the strength of the bond and continuity of the pores are adversely affected, or the fibrous tissue ingrowth impeded.

The mix should contain a suitable polymerization initiator. For this purpose, any free radical initiator as is commonly used for acrylic polymerization reactions is usable including organic peroxides such as benzoylperoxide, t-butylperoxide, hydroperoxides, persulfates, perborates, permanganates, azonitriles and organic hydroperoxides such as t-butylhydroperoxide.

In order to initiate the polymerization reaction and to control it, accelerators must be present. Suitable accelerators include organic bases such as dimethyl-p-toluidine and pyridine.

If a spontaneously decomposing peroxide such as t-butylhydroperoxide is used, a reducing agent accelerator should be used such as ferrous ion.

If cationic initiation of the polymerization reaction is used, a Lewis acid such as boron trifluoride should be used for the polymerization of, for example, 2-methylstryene, alkyl vinyl ethers and the like.

If the polymerization reaction is initiated by anionic polymerization catalysts, strong bases such as sodium amide and organometallic bases should be used.

Other initiating sources for the polymerization reaction include condensation polymerization catalysts as well as heat, ultraviolet radiation and high energy irradiation such as X-rays.

In order to use the composition for orthopedic or dental application, it is necessary to add a filler to raise the viscosity of the composition to a pliable, moldable paste. For this purpose, it is preferable to use an acrylic polymer, which may be formed from the same or different monomer as is used in the mix. The selection of acrylic polymers is preferred because it will readily cross-link with the polymer being formed and therefore will contribute to the strength and homogeneity of the product. Polymers of sufficiently high molecular weight should be used to render polymer diffusion from the bulk material in situ negligible. The filler polymers of course, must be non-toxic, non-carcinogenic, non-degrading and non-swelling in body fluids. The fillers must also be chemically stable, biologically inert and have mechanical qualities appropriate for restorative bone cements. Suitable polymer materials which may be used as fillers include the following, such as polymethylmethacrylate, polymethylmethacrylate-styrene copolymers polyethylmethacrylate and polymers of the appropriate monomers listed among the previously mentioned monomers as well as their stereo specific isomers and copolymers thereof.

The filler is used in an amount sufficient to form a dispersion or organosol of solid polymer in monomer liquid to bring the mix to paste-like consistency which is soft and pliable like a smooth paste or like a putty. For this purpose the filler may be used in an amount of 35 to 65% by weight of total composition, for filler particles having a particle size of less than 100μ and preferably less than 2μ. It has been found that the particle size and surface area of the filler is quite important for obtaining the proper consistency. The desired consistency may also be obtained by partial polymerization of the monomer, i.e., by stopping the polymerization reaction at an intermediate stage to form a high molecular weight, pliable material.

The mix is then applied to the bone parts or to a bone and a metal bone implant, or to a fractured tooth or bone and is polymerized in situ. Since the soluble particles act as a heat sink, exothermic heat generated by the reaction is taken up and a very careful control of the optimum temperature is possible. The presence of the particles and the filler also functions to reduce the quantity of monomer being polymerized by a dilution effect, which of course also have a favorable effect in keeping the exothermal heat generated low.

Following the polymerization, the crystals will dissolve in the extracellular fluid and leave behind pores in the acrylic cement bond. After the bond is formed, the soluble particles will be leached out over a probable period of several weeks. The actual time period during which the leaching occurs is clinically insignificant.

As discussed above, one of the crucial aspects of this invention is the discovery that as a result of the replacement of some of the cement bulk by soluble particles, the amount of monomer used in each procedure is proportionally reduced. This reduction is also reflected in the amount of monomer escaping to the central circulation. Moreover, due to the small sizes of the soluble particles, the total surface area of soluble particles is large. This surface area will absorb monomer molecules prior to their polymerization, thus contributing to the over-all reduction of monomers escaping from the bond site. As the absorbing layer is probably not more than one or two monomer molecules thick, the particles remain perfectly leachable.

The presence of continuous pores is expected to result in a significant loss in strength, but this is not so if the particles are used in the above quantity range. The extent of the strength loss, in fact, does not weaken the cement beyond clinical tolerance. Moreover, what strength loss does occur, would be expected to be regained as the fibrous tissue grows into the pores and through the bond interface.

Having now generally described the invention, a further understanding can be attained by reference to certain specific examples which are provided herein for purposes of illustration only and are not intended to be construed as limiting unless otherwise so specified.

EXAMPLE 1

Reduction in Polymerization Temperature and Thermal Necrosis

Sucrose crystals were admixed with Simplex P; a commercially available acrylic cement composed of 66% w/w powdered polymethylmethacrylate, 33% w/w methylmethacrylate-styrene copolymer, about 0.5% benzoylperoxide (initiator), about 2.6% N,N-dimethyl-p-toluidine (accelerator) and 97.4% v/v methylmethacrylate and 75 ppm hydroquinone in 20 ml liquid. In the first instance, the quantity of crystals was held constant, so that the variations in crystal to Simplex ratio was attributable to the variation in cement. FIG. 1 shows the reduction in polymerization temperature as a function of increasing percent of sucrose crystals.

EXAMPLE 2

Reduction of Monomer Migration Into the General Circulatory System Experimental 1. 9.1 grams of Simplex P was extruded — six minutes after mixing the components — through a ¼ inch nozzle into 30 ml of outdated human blood and kept there for fourteen more minutes. The blood was then poured off, beaker and sample rinsed with distilled water (which was added to the blood) and shaken in a separatory funnel with 30 ml of cyclohexane. This mixture was then transferred to high density polyethylene tubes and centrifugated at about 1000 R.P.M. for seven minutes. There were, after that, three layers. On top (a) clear cyclohexane, in the middle (b) a cyclohexane rich plasma layer and at the bottom (c) packed red blood cells.

First, layer (a) was pipetted off. The layers (b) and (c) were shaken again with another 30 ml of cyclohexane and centrifuged. Again layer (a) was removed and added to the first layer (a). Then the gel-like plasma layer (b) was removed and centrifuged with cyclohexane used to wash the funnel, etc. The clean cyclohexane layer on top was pipetted off and added to the previously collected cyclohexane layers. The rest was discarded. 2. The experimental steps of experimental (1) were repeated exactly, but this time using 12½% 120/140 mesh sugar in the cement, 7.2 grams U.V. Absorption at 215 mµ

Solution (1) was first diluted to a total of 100 ml. Then a small sample of this was diluted 50 times and measured against pure cyclohexane as reference. Read 39.0 units.

Solution (2) was also made up to 100 ml. A small sample of this diluted 50 times. Read 24.3 units with pure cyclohexane as reference.

The above results show that the presence of sucrose crystals caused a significant reduction in monomer migration.

EXAMPLE 3

The procedure of Example 2 was repeated except using tricalcium phosphate (TCP) instead of sucrose crystals. The U.V. absorption at 215 mµ was as follows:

| Weight of Sample, grams | %TCP | U.V. Absorbance |
|---|---|---|
| 5.0 | 0 | 72.0 |
| 7.1 | 0 | 91.4 |
| 11.3 | 0 | 137.0 |
| 4.7 | 12.5 | 75.0 |
| 6.9 | 12.5 | 87.2 |
| 12.1 | 12.5 | 137.7 |
| 3.6 | 37.5 | 42.2 |
| 7.2 | 37.5 | 68.0 |
| 10.5 | 37.5 | 81.1 |

There results show that the extent of monomer migration is inversely proportional to the weight of TCP present.

EXAMPLE 4

In Vivo Experiments

A dog about 30 pounds was prepared according to conventional test procedures for cement implantation. 20.8 g of Simplex P (cement) was prepared without the addition of crystals and a portion of the cement was inserted into a ⅛ inch diameter hole into the ilium near acetabulum and worked through, mushrooming at the other side. Implantation was complete within 6-½ minutes. 5 ml of blood samples were taken from the femoral vein before the junction with the femoral vien of the other leg at 7 minutes and 7½ minutes, and every minute thereafter until a total sample of 50 ml was obtained.

This experiment was repeated using the same cement except with the addition of 45% weight TCP. 21.3 g of the mixture was worked as above.

Blood samples were taken as above. The blood samples were extracted and subjected to U.V. analysis. The U.V. absorbance was as follows:

| | U.V. Absorbance |
|---|---|
| Control | 14.4 |
| No TCP | 84.3 |

| | U.V. Absorbance |
|---|---|
| 45% TCP | 27.6 |

A mutt dog weighing 27 pounds was subjected to the above treatment using 28.08 grams of plain cement, and 30.25 g of cement containing 25% weight sucrose. The U.V. readout was as follows:
Control; 17.2
No sucrose; 75.3
25% sucrose; 45.6

The addition of sucrose and TCP effected significant reduction in the quantity of monomer released.

EXAMPLE 5

Ingrowth of Fibrous and Bony Tissues

The ingrowth of fibrous and bony tissues by mixing various sucrose crystal percentages and sizes with the Simplex, was investigated prior to polymerization. Following implantation and hardening the sucrose will dissolve and leave behind a continuous pore system.

Plugs were implanted on fifty-two rabbit ilia. Three types of plugs were embedded: (1) those in which the sucrose crystals had been thoroughly mixed with the solid component, (2) those in which the plugs were rolled in sucrose crystals as soon as the dough became malleable, and (3) those with sucrose crystals mixed in as well as applied superficially.

As a control, plain acrylic cement (Simplex) was used in two ilia. Sucrose concentrations of 10, 20, 30, 40, 50 and 60 percent were used in the mixed samples. Three grades of sucrose crystal sizes were used, b 53–63$\mu$, 105–125$\mu$, and 250–297$\mu$. The rabbits were sacrificed at periods ranging from one day to nine months. A series of control rabbits were sacrificed at one to four days. The tissue ingrowth seen in the stained sections was rated on an arbitrarily chosen 1+ to 4+ scale.

No tissue growth was noted in the plugs from the control rabbits which had plain Simplex and in those plugs which were removed at one to four days. No or little (1+) tissue ingrowth was noted in the plugs with 10 and 20 percent sucrose. Much (3+ to 4+) tissue ingrowth was noted in the animals sacrified after thirty and sixty days at sucrose concentrations of 30, 40, 50 and 60 percent.

Histologically, the tissue appeared to be fibrous and osseous in nature, fairly cellular, and well stained with Van Gieson stain. The tissue occured in the lamellar arrangement characteristic of collagenous tissue. The tissue within the plugs also contained a large amount of hydroxyproline, an amino acid which appears only in collagen.

As expected, tissue ingrowth did not penetrate deeply into the plugs that were only superficially coated with sucrose crystals.

EXAMPLE 6

Effect of Porosity and Pore Size on the Strength of the Acrylic Resin

The diametral tensile strength (DTS) was tested using an Instron tensile testing machine. DTS measurements provide a convenient method for evaluation of tensile strengths of acrylic implants. The DTS can be directly calculated from the load at collapse and the dimensions of the cylindrical plugs. The results have indicated that unmodified Simplex resin is two to three times stronger than bone and about 15% stronger than roots of teeth. Consequently, a considerable percentage of porosity can be tolerated without impairing the strength factors beyond tolerance. Moreover, the strength will be increased as the tissue ingrowth occurs. These results show that the effect of pore size is small compared to that of percentage porosity. The results are shown in FIG. 2.

The porous cement of the invention can be used in the treatment of fractures and bone defects. A number of preliminary experiments have been carried out to investigate the usefulness of such applications. Sections from the tibia of rabbits have been segmentally resected for this purpose. Steinman pins, coated with acrylic dough containing sucrose crystals, were inserted into proximal and distal segments of the tibia. X-ray evidence shows that healing is satisfactory.

One of the greatest problems in the treatment of amputees has been the failure to develop devices which could be implanted into the amputee's limbs rather than using external fixation. The reason for failure in the development of such an implantable prosthesis has been the rejection at the skin-implant interface.

The porous acrylic cement of this invention also can find application in the fixation of artificial limbs in which epithelial cell growth occurs around tooth implants and artifical limbs.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. An osseous cement for orthopedic or dental application which comprises:

the admixture of 10–40% by weight of organic or inorganic particles leachable by the extracellular fluid of the host which are of particle size 50–250$\mu$ (average) and are present in an amount within said range of 10–40% such that they form a continuous pore system in the cement when leached from the cement in situ, 20–40% by weight of an acrylic monomer, 35–65% by weight of an insoluble particulate filler of negligible diffusion from the mixture which is non-toxic, non-carcinogenic, non-degrading, non-swellable in body fluids, chemically stable, biologically inert, has appropriate mechanical qualities so as to be capable of raising the viscosity of the composition to a pliable, moldable paste having a particle size of less than 100$\mu$, and a means for initiating polymerization of said acrylic monomer, wherein said leachable particles in addition:

1. have approximately the same pH as the extracellular fluid;
   2. have substantially no effect on the ionic strength of the extracellular fluid;
   3. are non-toxic;
   4. are hard and relatively non-deformable such that the particles maintain the proper size porosity of the deposited cement;
   5. have a melting point above the polymerization temperature of said acrylic monomer; and
   6. are not soluble or swellable in the monomer or subsequent polymer.

2. The osseous cement of claim 1, wherein the composition of the leachable particles is selected from the group consisting of monosaccharides, disaccharides, oligosaccharides, metabolites, organic acid salts, organic acid esters, and inorganic buffer salts which satisfy the requirements for said leachable particles specified in claim 1.

3. The osseous cement of claim 2, wherein the leachable particles are selected from the group consisting of calcium glycerate, sodium fumarate, calcium isovalerate, calcium nitrate, calcium succinate, calcium fumarate, $CaCo_3 \cdot MgCO_3$, calcium laurate, calcium glycerophosphate, calcium lactate, calcium saccharate, calcium salicylate, calcium carbonate, tricalcium phosphate, hydroxyapatite and calcium gluconate.

4. An osseous cement for orthopedic or dental application, which comprises:

the admixture of 10-40% by weight of organic or inorganic particles, leachable by the extracellular fluid of the host which are of particle size 50-250μ (average) and are present in an amount within said range of 10-40% such that they form a continuous pore system in the cement when leached from the cement in situ, 20-40% by weight of an acrylic monomer; 35-65% by weight of an insoluble particulate filler which is non-toxic, non-carcinogenic, non-degrading, non-swellable in body fluids, chemically stable, biologically inert, has appropriate mechanical qualities so as to be capable of raising the viscosity of the composition to a pliable, moldable paste, wherein said filler is an acrylic polymer of sufficiently high molecular weight to render polymer diffusion from the mixture negligible and having a particle size of less than 100μ, and a means for initiating polymerization of said acrylic monomer, wherein said leachable particles in addition:

1. have approximately the same pH as the extracellular fluid;
2. have substantially no effect on the ionic strength of the extracellular fluid;
3. are non-toxic;
4. are hard and relatively non-deformable such that the particles maintain the proper size porosity of the deposited cement;
5. have a melting point above the polymerization temperature of said acrylic monomer; and
6. are not soluble or swellable in the monomer or subsequent polymer.

5. The osseous cement of claim 4, wherein the particles are sucrose crystals.

6. The osseous cement of claim 4, wherein said leachable inorganic particle is tricalcium phosphate.

* * * * *